United States Patent [19]

Aker

[11] Patent Number: 4,998,974

[45] Date of Patent: Mar. 12, 1991

[54] APPARATUS AND METHOD FOR ANTITACHYCARDIA PACING IN DUAL CHAMBER ARRHYTHMIA CONTROL SYSTEM

[75] Inventor: David Aker, Elanora Heights, Australia

[73] Assignee: Telectronics Pacing Systems, Inc., Englewood, Colo.

[21] Appl. No.: 462,499

[22] Filed: Jan. 5, 1990

[51] Int. Cl.$^5$ .......................................... A61N 1/368
[52] U.S. Cl. ........................................... 128/419 PG
[58] Field of Search ................................ 128/419 PG

[56] References Cited

U.S. PATENT DOCUMENTS

| | | | |
|---|---|---|---|
| 3,857,398 | 12/1974 | Rubin | 128/419 D |
| 3,942,534 | 3/1976 | Allen et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,429,697 | 2/1984 | Nappholz et al. | 128/419 PG |
| 4,587,970 | 5/1986 | Holley et al. | 128/419 PG |

Primary Examiner—William E. Kamm
Assistant Examiner—Scott M. Getzow
Attorney, Agent, or Firm—Gottlieb, Rackman & Reisman

[57] ABSTRACT

Apparatus and method of antitachycardia pacing in a duel chamber pacing device including means for or steps of detecting the presence of a tachycardia, measuring the tachycardia cycle length, determining a VA interval value less than or equal to the tachycardia cycle length, determining an initial value of the AV delay interval, delivering pulses to the ventricle and to the atrium until the expiration of N VA intervals and N AV intervals thereby completing a first train of pulses, delivering a series of M trains of pulses similar to said first train pulses, and varying the AV delay interval value from the initial value at least once prior to the completion of the series of M trains of pulses. Monitoring of instrinsic QRS complexes between pulse trains is performed. If the tachyarrhythmia is deemed to be accelerating, one of cardioversion or defibrillation may be applied.

48 Claims, 6 Drawing Sheets

DUAL CHAMBER ANTITACHYCARDIA PACING ALGORITHM

```
TCL = 300 ms
VA  = 70% TCL
    = 210 ms

AV  = 10 ms
      50 ms
      100 ms
      150 ms
```

TRAIN 1 N=4

TRAIN 2 N=4

TRAIN 3 N=4

TRAIN 4 N=4

FIG. 5.
DUAL CHAMBER ANTITACHYCARDIA PACING ALGORITHM

TCL = 300 ms
VA = 80% TCL
= 240 ms

AV = 10 ms
50 ms
100 ms
168 ms

TRAIN 1 N=4

TRAIN 2 N=5

TRAIN 3 N=6

TRAIN 4 N=6

OVERDRIVE PACING (80% SI)

80% SI = 80% X 850 ms
= 680 ms
80% SI AV = 80% X 210 ms
= 168 ms
VA = 680 ms - 168 ms
= 512 ms

SI = PREVIOUS SINUS INTERVAL

SI AV = AV DELAY FOR SI

FIG. 6.

APPARATUS AND METHOD FOR ANTITACHYCARDIA PACING IN DUAL CHAMBER ARRHYTHMIA CONTROL SYSTEM

TECHNICAL FIELD

This invention relates to implantable medical devices which monitor the cardiac state of a patient by sensing the patient's intrinsic rhythm, atrial and ventricular tachycardia, atrial and ventricular fibrillation/flutter and which deliver therapy in the form of electrical energy to cardiac tissue in both chambers of the heart in an attempt to revert tachycardia and restore a normal sinus rhythm. More particularly, the invention relates to an apparatus and method for antitachycardia pacing (ATP) in a dual chamber arrhythmia control system. Although the invention may be incorporated in an antitachycardia pacing device alone, it is described herein as operating in a combined implantable antitachycardia pacing, bradycardia pacing, defibrillating or cardioverting arrhythmia control system.

As used herein, the term tachycardia refers to any fast abnormal rhythm of the heart which may be amenable to treatment by electrical discharges and specifically includes sinus tachycardia, supraventricular tachycardia (SVT), atrial tachycardia, (AT), atrial fibrillation and flutter (AF), ventricular tachycardia (VT), ventricular flutter and ventricular fibrillation (VF).

PRIOR ART

U.S. Pat. No. 3,857,398 to Rubin describes a combined pacer/defibrillator. This device either performs a bradycardia pacing or a defibrillation function depending on the detection of a VT/VF. If a VT/VF is detected, the device is switched to the defibrillating mode. After a period of time to charge the capacitor, a defibrillation shock is delivered to the patient.

Improvements on this device were contained in a multiprogrammable, telemetric, implantable defibrillator which is disclosed in copending patent application Ser. No. 239,624 entitled "Reconfirmation Prior to Shock in Implantable Defibrillator". The device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached.

As cardioversion or defibrillation shocks can be very unpleasant to a patient, especially when delivered frequently, it became necessary therefore to provide a device which included antitachycardia pacing therapy along with bradycardia support pacing therapy and defibrillation or cardioversion therapy, so that the implanted device could automatically provide the necessary therapy from a range of therapies offered by the device. Hence a further development in the field of combined implantable devices is described in copending U.S. patent application Ser. No. 187,787, to Grevis and Gilli, filed Apr. 29, 1988, and entitled "Apparatus and Method for Controlling Multiple Sensitivities in Arrhythmia Control Systems Including Post Therapy Pacing Delay", assigned to the assignee of the present invention. This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient.

Additionally, various specific developments have been made in the field of tachycardia control pacers. Tachycardia is a condition in which the heart beats very rapidly; with a ventricular rate higher than 100 bpm and typically above 150 bpm and an atrial rate as high as 400 bpm. There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback within the heart. A natural beat results in the feedback of an electrical stimulus which prematurely triggers another beat. By interposing a stimulated heartbeat, the stability of the feedback loop is disrupted.

In U.S. Pat. No. 3,942,534 to Spurrell et al. there is disclosed a pacer which, following detection of a tachycardia, generates an atrial (or ventricular) stimulus after a delay interval. If that stimulus is not successful in terminating the condition, then another stimulus is generated after another premature heartbeat following a slightly different delay. The device constantly adjusts the delay interval by scanning through a predetermined delay range. Stimulation ceases as soon as the heart is restored to sinus rhythm. If successful reversion is not achieved during one complete scan, then the cycle is repeated. The device further provides a second stimulus following the first, both stimuli occurring within the tachycardia cycle, i.e. before the next naturally occurring rapid beat. The time period between a heartbeat and the first stimulus is known as the initial delay, while the time period between the first stimulus and the second stimulus is known as the coupled interval. In this device, once the coupled interval is set by a physician it is fixed, and therefore the second stimulus always occurs a predetermined time after the first stimulus, no matter when the first stimulus occurs after the last heartbeat or how fast is the rate of the tachycardia.

In U.S. Pat. No. 4,390,021 to Spurrell et al. there is disclosed a pacer for controlling tachycardia in which the coupled interval, as well as the initial delay, is scanned. The time parameters which are successful in terminating the tachycardia are stored so that upon confirmation of another tachycardia event, the previously successful time parameters are the first ones to be tried. The device also allows tachycardia to be induced by the physician to allow for programming of the initial delay and the coupled interval parameters.

U.S. Pat. No. 4,398,536 to Nappholz et al. discloses a scanning burst tachycardia control pacer. Following each tachycardia confirmation, a burst of a programmed number of stimulating atrial (or ventricular) pulses is generated. The rates of the bursts increase from cycle to cycle whereby following each tachycardia confirmation, a pulse burst at a different rate is generated. The rate of a burst which is successful in terminating tachycardia is stored, and following the next tachycardia confirmation, the stored rate is used for the first burst which is generated.

In U.S. Pat. No. 4,406,287 to Nappholz et al. there is disclosed a variable length scanning burst tachycardia control pacer. The physician programs the maximum number of pulses in a burst. The number of pulses in a burst is scanned, and the number which is successful in terminating tachycardia is registered so that it is available for first use when a new tachycardia episode is confirmed. Successive bursts, all at the same rate, have different numbers of pulses, the pulse number scanning being in the upward direction. If all bursts are unsuccessful, a new rate is tried and the number scanning begins over again. Thus all combinations of rates and pulse numbers are tried, with the successful combination being used first following the next tachycardia confirmation.

U.S. Pat. No. 4,408,606 to Spurrell et al. discloses a rate related tachycardia control pacer. Following tachycardia confirmation, a burst of at least three stimulating pulses is generated. The time intervals between successive pulses decrease by a fixed decrement; hence the rate of the pulses increases during each cycle of operation. The first pulse is generated following the last heartbeat which is used to confirm tachycardia at a time which is dependent on the tachycardia rate. The time delay between the last heartbeat and the first pulse in the burst is equal to the time interval between the last two heartbeats less the fixed decrement which characterizes successive time intervals between stimulating pulses.

Dual chamber heart pacers have been developed in order to generate sequential atrial and ventricular pacing pulses which closely match the physiological requirements of the patient. A conventional dual chamber heart pacer as disclosed in U.S. Pat. No. 4,429,697 to Nappholz et al. includes atrial beat sensing and pulse generating circuits along with ventricular beat sensing and pulse generating circuits. It is known that the detection of a ventricular beat or the generation of a ventricular pacing pulse initiates the timing of an interval known as the VA delay. If an atrial beat is not sensed prior to expiration of the VA delay interval, then an atrial pacing pulse is generated. Following the generation of an atrial pacing pulse, or a sensed atrial beat, an interval known as the AV delay is timed. If a ventricular beat is not sensed prior to the expiration of the AV delay interval, then a ventricular pacing pulse is generated. With the generation of a ventricular pacing pulse, or the sensing of a ventricular beat, the VA delay timing starts again. This patent describes how the VA delay timing interval may be divided into three parts; the atrial refractory period, the Wenckeback timing window, and the P-wave synchrony timing window. It outlines the importance of controlling the ventricular rate in comparison with the atrial rate in order to maintain synchrony between the atrium and the ventricle. The patent does not however address the issue of antitachycardia pacing therapy.

Prior art single chamber antitachycardia pacing devices which provide antitachycardia pacing bursts to either the atrium or the ventricle, have shortcomings in that they lack the required synchrony between the atrium and the ventricle, which reduces the percentage of successful reversions. Especially in the case of ventricular antitachycardia pacing, although the pacing may revert an arrhythmia, at the same time however, it increases the risk of adversely affecting the patient by means of a decrease in arterial pressure due to the rapid pacing. As a result of the haemodynamic compromise or lowered haemodynamic status of the myocardium during the arrhythmia and pacing, there is a high risk of a ventricular tachycardia accelerating to a faster ventricular tachycardia and even to a ventricular fibrillation. This has been shown in an article by Fisher et al. entitled "Termination of Ventricular Tachycardia with Burst or Rapid Ventricular Pacing", American Journal of Cardiology, Vol. 41 (January, 1978), page 96. Not only does this present a potentially hazardous situation to the patient, but it also makes it more difficult for the device to revert the patient. Reversion would necessarily demand more energy of the device and perhaps even cardioversion or defibrillation therapy which is not available in many pacing devices. Furthermore, prior art devices are very limited in the provision of individualized therapy to the patient by patient dependent parameters such as the AV delay.

Many antitachycardia pacing therapy devices at present include defibrillation support within the device in order to provide adequate safety to a patient. It is highly advantageous to prevent the development of VT's or atrial fibrillations or to terminate them quickly if they appear, rather than allowing the arrhythmia to develop to such an extent that a defibrillation shock is necessary.

DISCLOSURE OF THE INVENTION

It is an object of the invention to provide antitachycardia pacing therapy in an automatic implantable device with an improvement in patient safety by ensuring that the patient maintains an improved haemodynamic status during application of the antitachycardia pacing therapy as compared to prior devices.

It is a further object of the invention to provide synchrony between the atrium and the ventricle during antitachycardia pacing therapy so that the arterial pressure is either maintained or increased during the therapy.

It is a further object of the invention to increase the opportunities for antitachycardia pacing therapy by means of a reliable low risk energy saving therapy with a higher chance of faster and more successful reversion.

It is a further object of the invention to reduce the number or the necessity of defibrillation shocks given to a patient by preventing the development of VT's and AF's in a patient by means of a more effective dual chamber antitachycardia pacing algorithm.

It is a further object of the invention to provide a means during the application of dual chamber antitachycardia pacing therapy for the detection of inherent QRS complexes and a further means for providing cardioversion or defibrillation therapy if the detected QRS complexes meet programmed x/y and tachycardia cycle length criteria, in order to detect acceleration to VF's or fast VT's.

It is a further object of the invention to individualize the antitachycardia pacing therapy to each patient in an automatic implantable dual chamber arrhythmia control system by means of programming parameters such as the AV delay as a percentage of the tachycardia cycle length.

According to the invention, there is provided a dual chamber antitachycardia pacing device for the reversion of tachycardias comprising: means for detecting tachycardia, means for measuring cycle length of said tachycardia, means for determining a VA interval value less than or equal to the tachycardia cycle length, means for determining an initial value AV delay interval, pulse generating means responsive to said tachycardia detecting means for generating heart stimulating pulses to the atrium and to the ventricle, said pulse generating means including means for delivering a series of M pulse trains with each train consisting of a total of 2N pacing pulses delivered in an alternating sequence to the ventricle and to the atrium, the timing of said delivered pulses being in accordance with the values of the VA interval and the AV interval whereby each train comprises the delivery of a pacing pulse to the atrium at the expiration of each of N VA delay intervals and a pacing pulse to the ventricle at the expiration of each of N AV delay intervals, and means for varying the AV delay interval from the initial value at least once prior to completion of the series of M pulse trains. The apparatus may also include confirmation means for confirming the presence of the tachycardia prior to enabling the pulse generating means. In this case the pulse generating means is responsive to the confirmation means.

Also in accordance with the invention, the device may include means for sensing inherent QRS complexes during the time between delivery of the pacing pulse trains, means for determining an acceleration cycle length value less than the tachycardia cycle length, means for measuring cycle length of the sensed QRS complexes, and means for delivering at least one of cardioversion and defibrillation when a number of cycle lengths of the sensed QRS complexes are less than the acceleration detection cycle length.

According to the invention, there is further provided a method of antitachycardia pacing in a dual chamber pacing device comprising the steps of: detecting the presence of a tachycardia, measuring the tachycardia cycle length, determining a VA interval value less than or equal to the tachycardia cycle length, determining an initial value of the AV delay interval, delivering a pulse to the ventricle, delivering a pulse to the atrium at the expiration of the determined VA interval value, delivering a pulse to the ventricle at the expiration of the AV interval value, repeating pulse delivery to the atrium and the ventricle until the expiration of N VA intervals and N AV intervals thereby completing a first train of pulses, delivering a series of M trains of pulses similar to said first train of pulses, varying the AV delay interval value from the programmed initial value at least once prior to the completion of the series of M trains of pulses. The method may also include the step of confirming the presence of tachycardia prior to delivery of the antitachycardia pacing pulses.

The method of the invention may also include the steps of sensing inherent QRS complexes during the time between the delivery of the trains of pacing pulses, determining an acceleration detection cycle length value less than the tachycardia cycle length, measuring cycle lengths of the sensed QRS complexes, and delivering at least one of cardioversion and defibrillation when a number of the cycle lengths of the sensed QRS complexes are less than the acceleration detection cycle length.

BRIEF DESCRIPTION OF THE DRAWINGS

Further objects, features and advantages of the invention will become apparent upon consideration of the following detailed description in conjunction with the drawings in which.

BEST MODE FOR CARRYING OUT THE INVENTION

Figure 1:
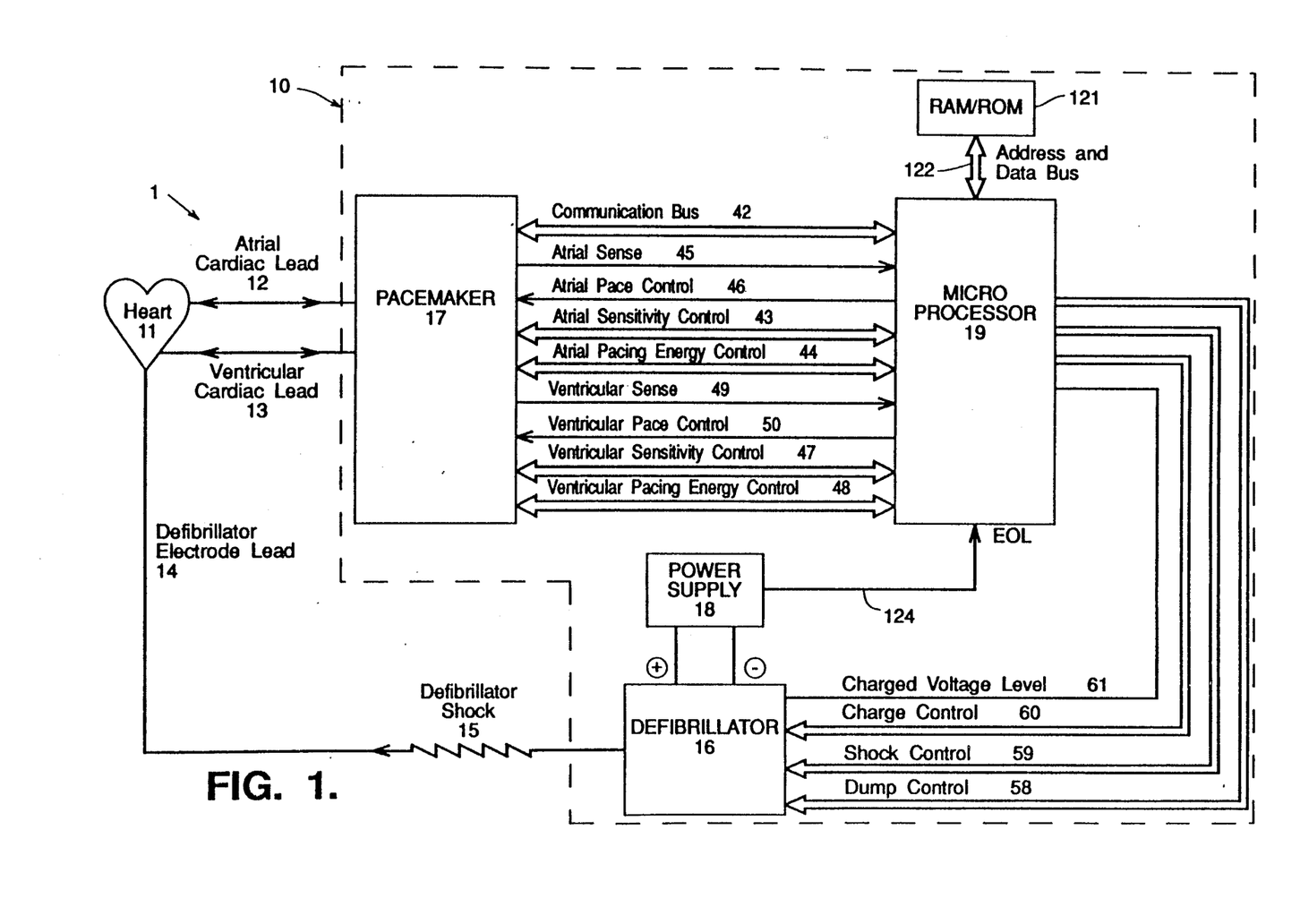
FIG. 1 is a block diagram of a dual chamber arrhythmia control system (ACS)

Referring to FIG. 1, there is depicted a block diagram of an arrhythmia control system 1. System 1 is designed to be implantable in a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium and a ventricular cardiac lead 13 extending to the ventricle of the patient's heart for the administration ministration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to both pacemaker 17 and defibrillator 16; and a power supply 18 for the provision of a reliable voltage level to pacemaker 17, microprocessor 19 and defibrillator 16 by suitable electrical conductors (not shown). Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

Microprocessor 19 is connected to a RAM/ROM unit 121 by an address and data bus 122. An end-of-life (EOL) signal line 124 is used to provide, to microprocessor 19, a logic signal indicative of the approach of battery failure in power supply 18.

As more fully described below, microprocessor 19 and pacemaker 17 are connected by a communication bus 42, an atrial sense line 45, an atrial pace control line 46, an atrial sensitivity control bus 43, an atrial pace energy control bus 44, a ventricular sense line 49, a ventricular pace control line 50, a ventricular sensitivity control bus 47, and a ventricular pace energy control bus 48. As also more fully described below, microprocessor 19 is connected to defibrillator 16 by a charged voltage level line 61, a charge control bus 60, a shock control bus 59, and a dump control bus 58.

Figure 2:
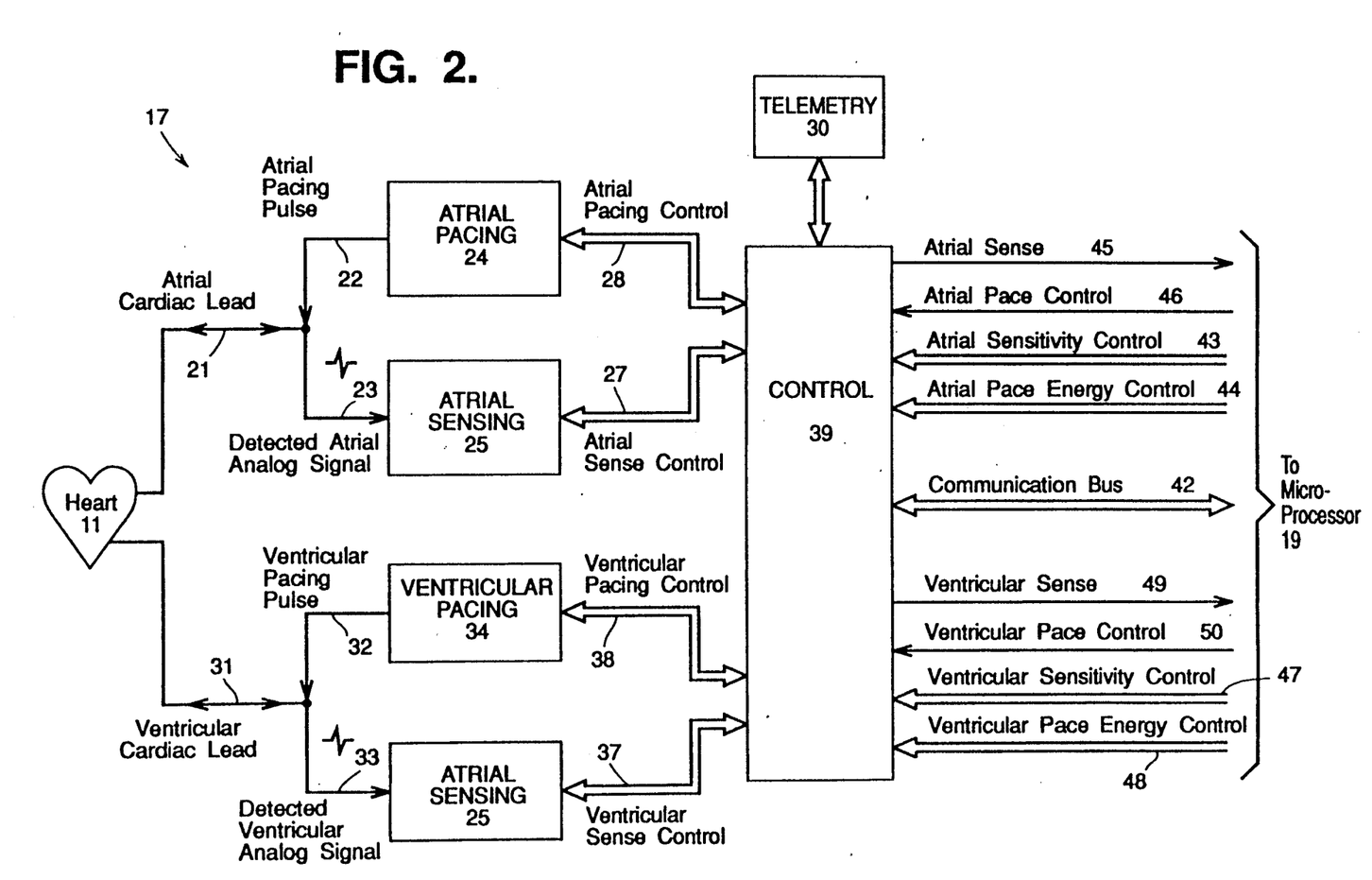
FIG. 2 is a block diagram of the pacemaker of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity will affect the voltage deviation required at the sensing electrode for a sense to be registered. The operation of the logic which changes the sensitivity is described in greater detail in copending U.S. patent application Ser. No. 187,797 of Richard Grevis and Norma Louise Gilli, filed Apr. 29, 1988, entitled "Apparatus And Method For Controlling Multiple Sensitivities In Arrhythmia Control System Including Post Therapy Pacing Delay," which is assigned to the assignee of the present invention and is incorporated herein by reference.

Atrial pacing circuit 24 receives from control block 39 via an atrial pacing control bus 28 an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in greater detail in U.S. Pat. No. 4,869,252 of Norma Louise Gilli, issued Sep. 26, 1989, entitled "Apparatus And Method For Controlling Pulse Energy In Antitachyarrhythmia And Bradycardia Pacing Devices," which is assigned to the assignee of the present invention and is incorporated herein by reference.

Telemetry circuit 30 provides a bidirectional link between control block 39 of pacemaker 17 and an external device such as a programmer. It allows data such as the operating parameters to be read from or altered in the implanted module 10.

Figure 3:
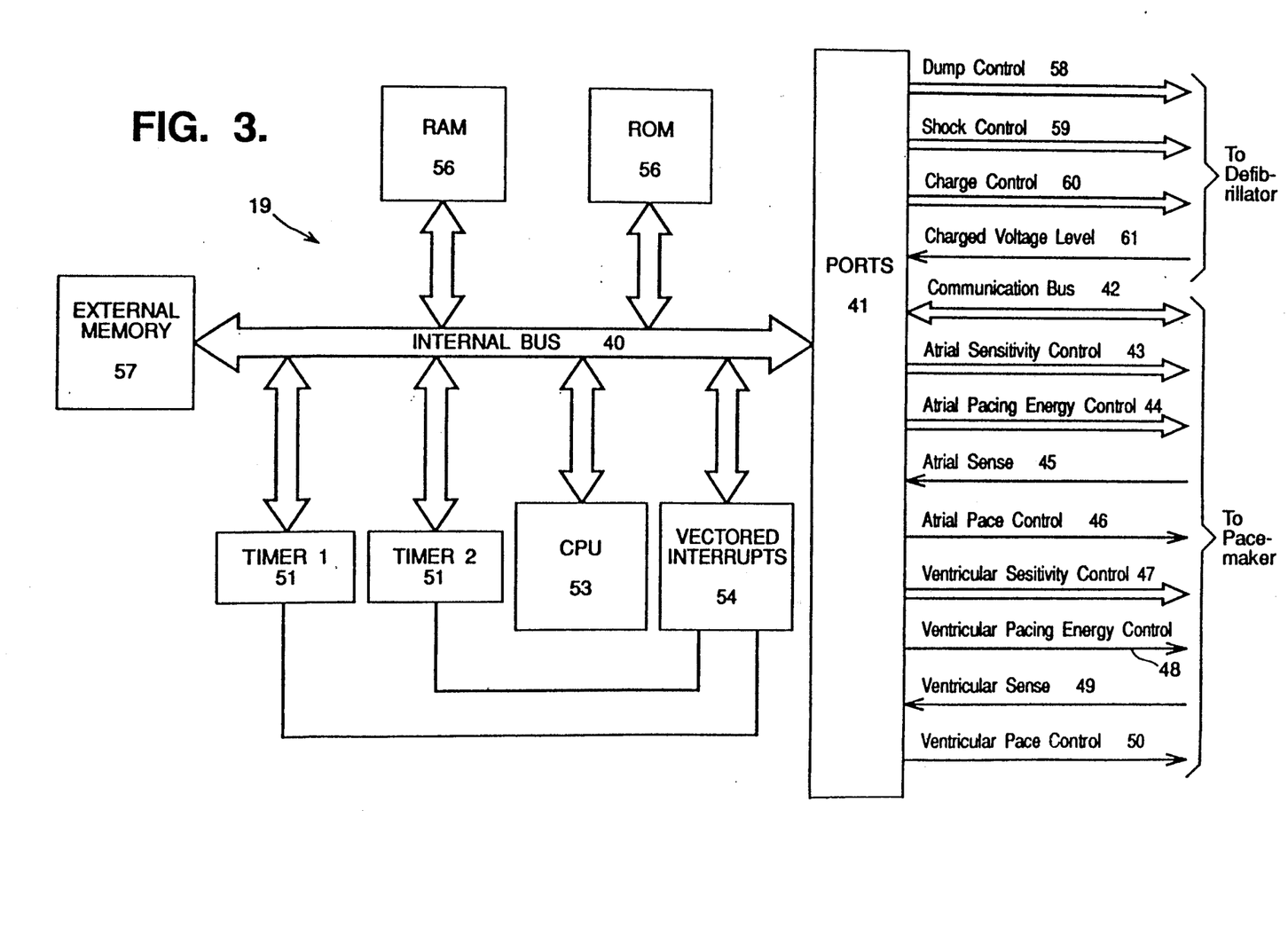
FIG. 3 is a block diagram of the microprocessor of FIG. 2.

Referring to FIG. 3, microprocessor 19 comprises two 16-bit timers 51 and 52, CPU 53, vectored interrupts block 54, ROM 55, RAM 56, external memory 57, ports 41 and an internal communications bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic flow diagram of FIG. 6, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 permit an external programmer (not shown) to change the operating parameters of pacemaker 17 by supplying appropriate signals to control block 39. Communications bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communications bus 42, through control block 39 in pacemaker 17, and into telemetry circuit 30 for transmission to the external programmer by a transmitter in telemetry circuit 30.

Microprocessor 19 receives various status and/or control inputs from pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on lines 44 and 48, respectively, which determine the magnitude of the pulse energy, the shock control on line 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. Charge voltage level line 61 provides a digital signal representative of charge voltage from an analog-to-digital converter within defibrillator 16, thus providing a feedback loop which assures that a shock of proper energy level is delivered by defibrillator 16.

Figure 4:
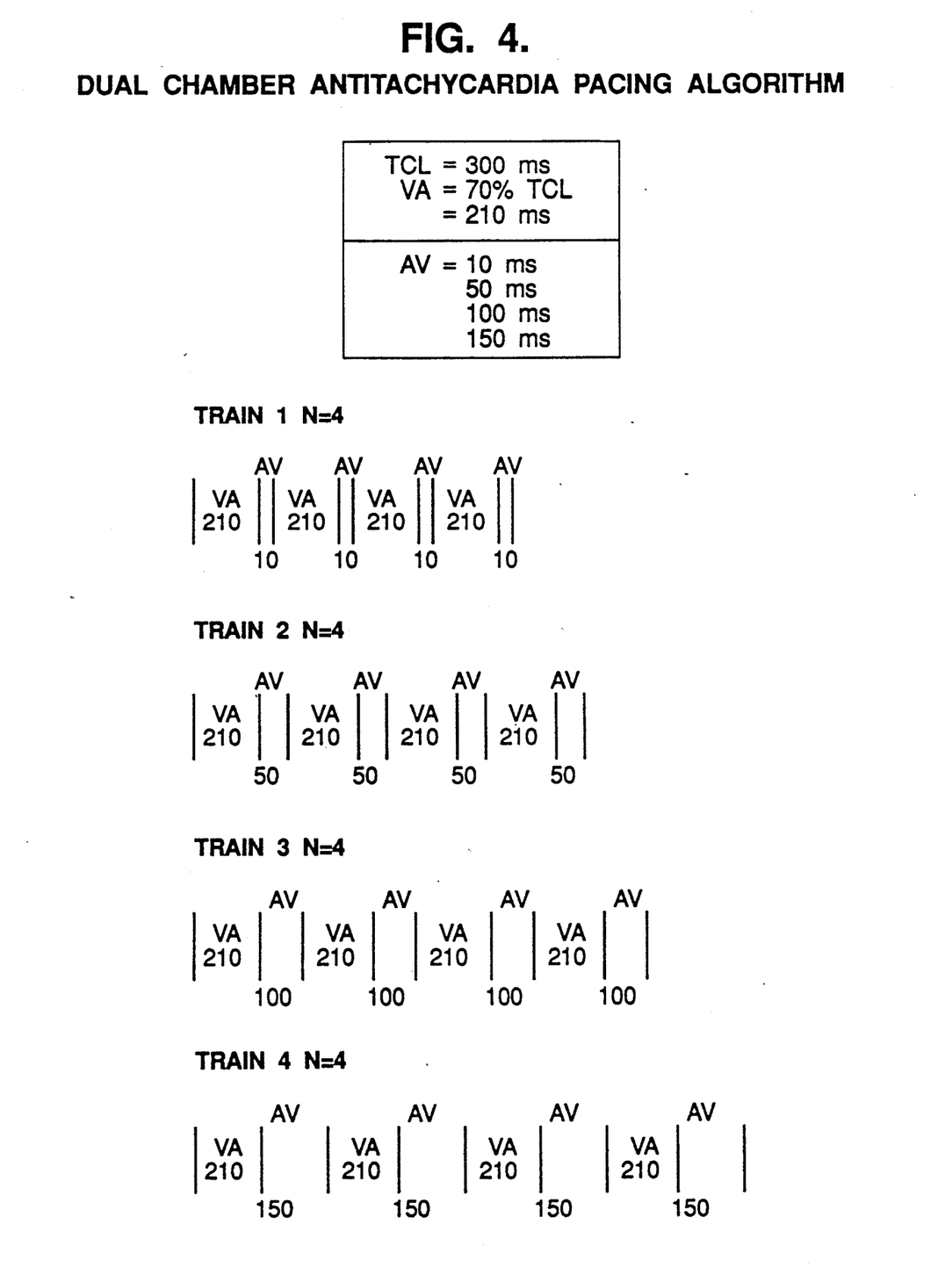
FIG. 4 illustrates an embodiment of the antitachycardia pacing algorithm according to the invention.

Referring to FIG. 4, there is depicted in illustrative format one embodiment of the antitachycardia pacing algorithm according to the invention. A series of M (M=4) pacing trains (a pacing train is a series of pacing spikes controllably delivered in rapid succession) are delivered. For train 1, the programmed initial AV delay (the atrial to ventricular delay) interval is 10 ms. During a ventricular tachycardia the atrium and the ventricle are often in dissociation, therefore it is preferable for the dual chamber antitachycardia pacing to begin with a very short AV delay interval in order to re-establish association or synchrony as soon as possible between both chambers of the heart. The tachycardia cycle length (TCL) is 300 ms. The VA delay interval (the ventricular to atrial interval) is calculated as a programmable percentage of the TCL for the purpose of adapting to the varying cycle lengths of tachycardias, and has been programmed to seventy percent of the TCL (300 ms) in this embodiment, thereby establishing the calculated VA delay interval as 210 ms. In this embodiment, the percentage of the TCL is taken as an average over the four previous sensed intervals, and remains fixed at this value (210 ms) during the course of the therapy. For train 1, N=4, so that at the expiration of each of the 4 VA delay intervals of 210 ms, an atrial pulse is delivered and at the expiration of each of the four AV delay intervals of 10 ms a pulse is delivered to the ventricle, so that there are a total of N pairs of pulses (or 2N=8 pulses) delivered during train 1.

In train 2 of FIG. 4, the AV delay interval has been programmed to increment in value from the low initial value of 10 ms in train 1 to the new value of 50 ms. The variation of the AV delay interval is executed by computer software by standard methods known to those skilled in the art. In the same manner in trains 3 and 4 of FIG. 4, the AV delay interval increases at the end of trains 2 and 3 to the increased values of 100 ms and 150 ms, respectively. In trains 2, 3, and 4, N=4, as in train 1, thereby delivering N (4) pairs of pacing pulses in each train. In this particular embodiment of the invention, the value of N is equal in all of the trains. However, N is a programmable parameter and may be programmed by the physician to suit the needs of a particular patient. Furthermore, N may have differing values for different trains in alternate embodiments of the invention.

As shown in FIG. 4, the AV delay interval increments from 10 ms in train 1 to 150 ms in train 4. This parameter is also programmable and is patient dependent. The AV delay may increment at the end of each train as in the preferred embodiment. However, the variation in the AV delay is not necessarily limited to steady increments. It may include any combination of increases, plateaus and decreases in its value. Although it is preferable to include the variations at the end of each train, these may be executed at any time within a train and still fall within the scope of the invention.

Preferably, the initial value AV delay interval is less than or equal to 60 ms.

The VA delay interval in the preferred embodiment is programmed as a percentage of the TCL (70%). Although the invention does not limit the VA delay interval to a particular range, it has been found that the best results occur when it lies within the range of thirty percent to one hundred percent of the TCL. Furthermore, its value is not necessarily fixed during the antitachycardia therapy, but may vary and still remain within the scope of the invention. If it is programmed to vary, the initial value is a percentage of the TCL; for example a percentage of the average cycle length of the last four intervals of the detected tachycardia. For instance, the VA delay interval may include various combinations of increasing, decreasing, or remaining at a fixed value. Any programmed variations may occur at the end of trains or even within trains, or may even be a function of AV delay interval variations.

In FIG. 4 the number of trains M is 4, and is also a patient dependent physician programmable parameter. At the completion of the M trains of antitachycardia pacing, the combined defibrillator pacing device returns to its normal operating mode including the options of normal dual chamber (DDD) pacing or defibrillation shocks, if necessary. Furthermore, the device may provide bradycardia support pacing, if required, which may include either single chamber or dual chamber bradycardia support pacing.

Figure 5:
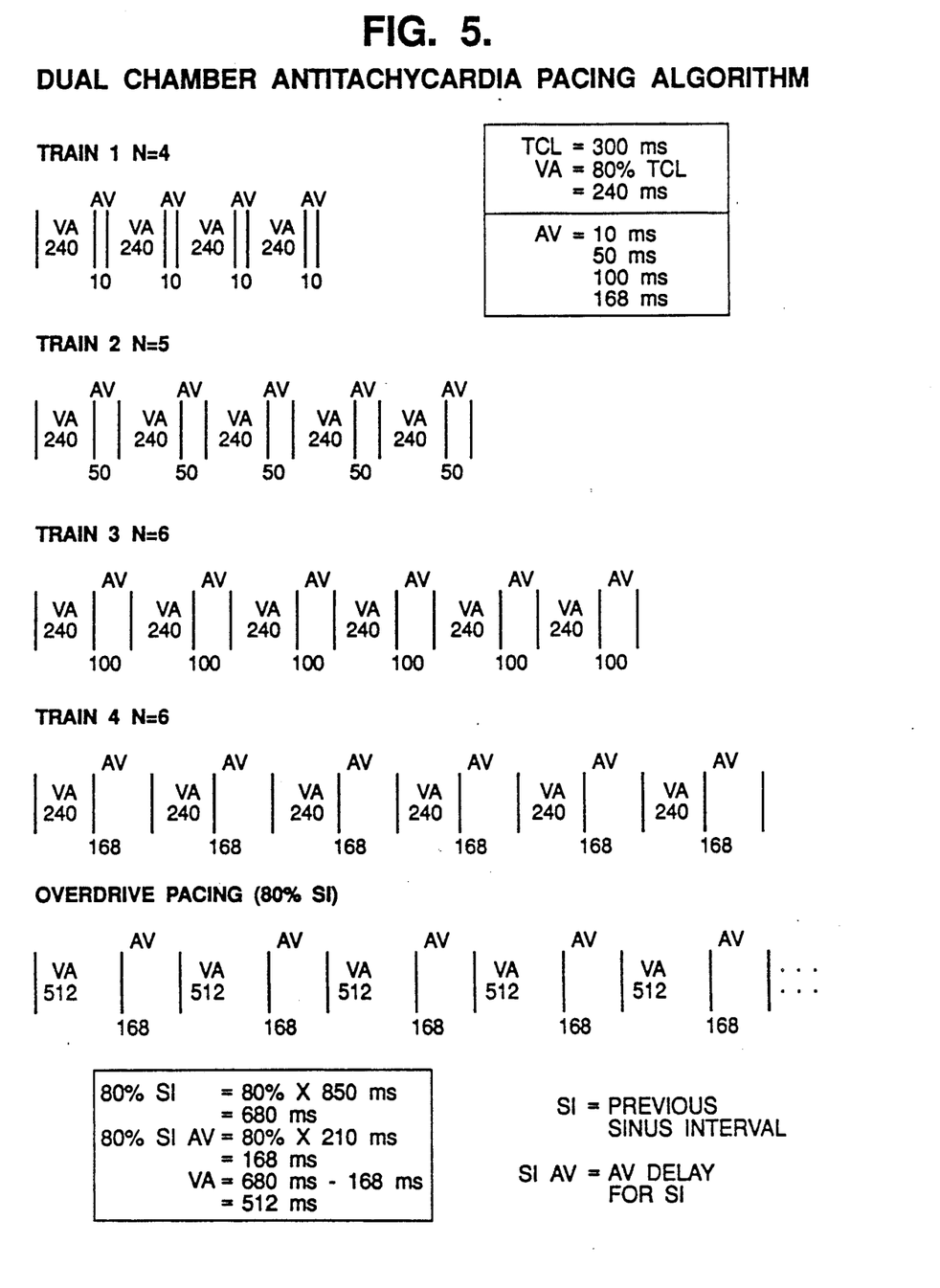
FIG. 5 illustrates a further embodiment of the dual chamber antitachycardia pacing algorithm according to the invention incorporating overdrive antitachycardia pacing.

In FIG. 5 there is shown another embodiment of the dual chamber antitachycardia pacing algorithm. The TCL is measured at 300 ms. The VA interval is programmed to be eighty percent of the TCL, and therefore assumes the value of 240 ms.

The AV delay is programmed to increment in value over 4 trains, and assumes the values of 10 ms (train 1), 50 ms (train 2), 100 ms (train 3), and 168 ms (train 4). In this embodiment, the value of N varies from N=4 in train 1, to N=5 in train 2, and then to N=6 in trains 3 and 4. The average sinus interval is measured prior to a tachycardia and is shown as the previous sinus interval or SI. In this example SI=850 ms. The AV delay for the previous sinus interval is measured also, and is known as SI AV, and is 210 ms in this example. The value of AV delay in train 4 is programmed to be eighty percent of SI AV, which is eighty percent of 210 ms, or 168 ms. The reason for including this value in train 4 is that following the final train, the device implements overdrive antitachycardia pacing at intervals of eighty percent of the intervals of SI in order to "ramp down" prior to the resumption of normal pacing. In this example eighty percent of SI is equal to eighty percent of 850 ms or 680 ms. This becomes the R—R interval for the overdrive pacing. The value of VA is set equal to the R—R interval minus the AV delay for the overdrive pacing, i.e. VA=680 ms-168 ms=512 ms. The time period for the overdrive pacing is programmable, and in this example it continues for five minutes prior to returning to normal pacing mode.

Figure 6:
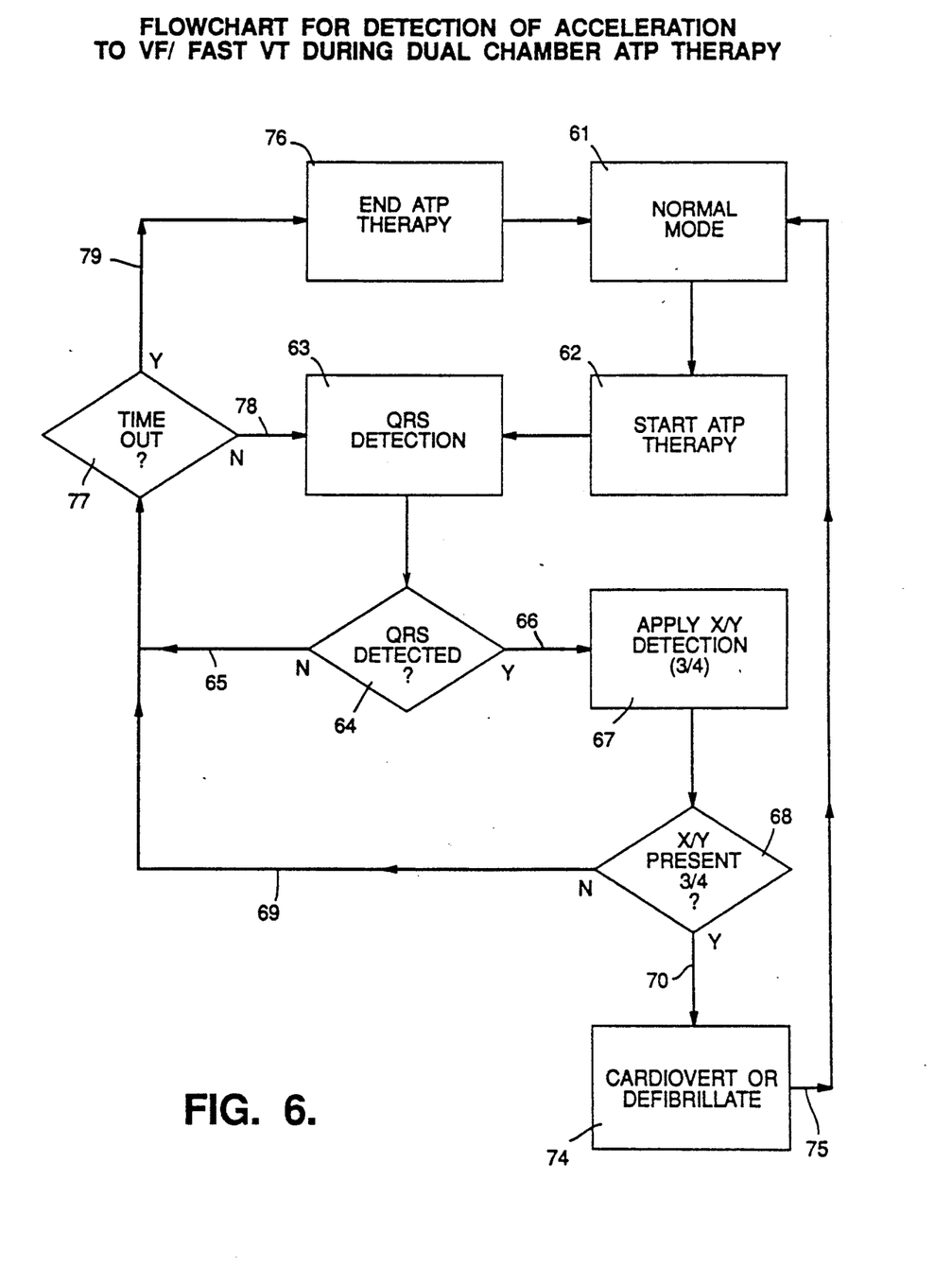
FIG. 6 is a flow chart for detection of acceleration to VF/fast VT during dual chamber antitachycardia pacing therapy.

FIG. 6 is a flowchart for the detection of acceleration to a VF or a fast VT during the application of the dual chamber antitachycardia pacing therapy. At 61, normal operating mode is shown and upon the detection of tachycardia and its subsequent confirmation (the details of this are not shown on the flow chart), the dual chamber ATP therapy is applied at 62. It is important, as a safety mechanism for the patient, during the application of any antitachycardia therapy, to prevent acceleration of VT to faster VT or to VF. QRS detection is switched on at 63 during the ATP therapy to detect inherent QRS complexes which may occur either during the VA interval or during the AV delay. A decision is made at 64 on the basis of whether QRS complexes are detected. If no QRS complexes are detected (65), control passes to timeout 77. If time is out (79), i.e. if the programmed time for the dual chamber ATP therapy has expired, then control passes to 76, the end of ATP therapy, and normal operating mode is resumed at 61. If at 77 the time has not expired (78), QRS detection at 63 is again commenced.

If there is detection of QRS complexes at 66, the next step is 67, where x/y detection is applied to determine whether the QRS complexes are regular or whether they are just isolated intrinsic beats. An example of x/y detection, in this embodiment, is ¾ detection. The acceleration detection window is programmable to an interval less than the detected tachycardia cycle length by an amount delta (300 ms in the examples of FIG. 4 and FIG. 5). Delta is programmable, and may be an absolute value or a percentage of the TCL. If delta is programmed to 75 ms, then 300 ms−75 ms=225 ms. Thus, the acceleration detection window becomes 225 ms. The acceleration detection interval is considered sufficient to detect an acceleration of an existing tachycardia. The ¾ detection means that if any three out of the last four intervals are less than the acceleration detection window (225 ms), then the x/y detection criteria are satisfied.

At 68, a decision is made to determine if the ¾ detection criterion applies to the QRS complexes. If the ¾ detection criterion is not met (69), control passes back to timeout at 77. If the time for therapy has not expired (78), it passes back to QRS detection at 63 and then either back to timeout 77 if no QRS complexes are detected at this time, or back to the application of x/y detection at 67 if QRS complexes are detected.

If at 70, the ¾ detection criterion has been met, cardioversion or defibrillation therapy is applied at 74. It has been found safer and more effective to use this acceleration detection combined with cardioversion or defibrillation therapy as shown in FIG. 6 than to wait until the end of ATP therapy and face the possibility of a degeneration to a very fast VT or a VF. After cardioversion or defibrillation therapy at 75, the device returns to its normal mode of operation at 61.

Although the invention has been described with reference to a particular embodiment, it is to be understood that this embodiment is merely illustrative of the application of the principles of the invention. Hence numerous modifications may be made therein and other arrangements may be devised without departing from the spirit and scope of the invention.

What is claimed is:

1. A dual chamber antitachycardia pacing device for the reversion of tachycardias in a heart comprising: means for detecting tachycardia, means for measuring cycle length of said tachycardia, means for determining a VA interval value less than or equal to the tachycardia cycle length, means for determining an initial value AV delay interval, pulse generating means responsive to said tachycardia detecting means for generating heart stimulating pulses for the atrium and for the ventricle, said pulse generating means including means for delivering a series of M pulse trains with each train consisting of a total of 2N pacing pulses delivered in an alternating sequence to the ventricle and to the atrium, so that timing of said delivered pulses is in accordance with the values of the VA interval and the AV interval, whereby each train comprises the delivery of a pacing pulse to the atrium at the expiration of each of N VA delay intervals and a pacing pulse to the ventricle at the expiration of each of N AV delay intervals, and means for varying said AV delay interval from said programmed initial value at least once prior to completion of said series of M pulse trains.

2. A dual chamber antitachycardia pacing device according to claim 1 further comprising means for confirming the presence of a tachycardia, wherein said pulse generating means is responsive to said confirming means.

3. A dual chamber antitachycardia pacing device according to claim 1 wherein said determined VA interval is a percentage of the tachycardia cycle length.

4. The dual chamber antitachycardia pacing device according to claim 3 wherein said percentage of the tachycardia cycle length is in the range of thirty to one hundred percent.

5. A dual chamber antitachycardia pacing device according to claim 1 further comprising means for incrementing said initial value AV delay interval at least once prior to said completion of said series of pulse trains to a final value AV delay interval.

6. A dual chamber antitachycardia pacing device according to claim 5 further comprising means for storing an average AV delay during previous sinus rhythm, wherein said final value AV delay interval is a function of and equal to or less than one hundred percent of the previous stored average AV delay during sinus rhythm.

7. A dual chamber antitachycardia pacing device according to claim 1 including means for providing dual chamber overdrive pacing at the completion of said M trains of pulses.

8. A dual chamber antitachycardia pacing device according to claim 7 further comprising means for programming a duration of said dual chamber overdrive pacing.

9. A dual chamber antitachycardia pacing device according to claim 7 further comprising means for storing an average AV delay during previous sinus rhythm, wherein said overdrive pacing includes an AV delay interval which is a function of and less than or equal to one hundred percent of the previous stored average AV delay during sinus rhythm.

10. A dual chamber antitachycardia pacing device according to claim 7 further comprising means for storing an average AV delay during previous sinus rhythm, wherein said dual chamber overdrive pacing includes a VA interval which is a function of and less than or equal to one hundred percent of the previous stored average VA delay interval during sinus rhythm.

11. A dual chamber antitachycardia pacing device according to claim 1 wherein said determined VA interval remains fixed during said series of M trains.

12. A dual chamber antitachycardia pacing device according to claim 1 further comprising means for varying said determined VA interval during the series of M trains.

13. A dual chamber antitachycardia pacing device according to claim 1 wherein said initial value AV delay interval is less than 20 ms.

14. A dual chamber antitachycardia pacing device according to claim 1 wherein said initial value AV delay interval is less than or equal to 60 ms.

15. A dual chamber antitachycardia pacing device according to claim 1 wherein N is fixed during said series of M trains.

16. A dual chamber antitachycardia pacing device according to claim 15 wherein N is between 1 and 10.

17. A dual chamber antitachycardia pacing device according to claim 1 further comprising means for varying N during said series of M trains.

18. A dual chamber antitachycardia pacing device according to claim 16 wherein N is between 1 and 10.

19. A dual chamber antitachycardia pacing device according to claim 1 wherein M is between 1 and 100.

20. A dual chamber antitachycardia pacing device according to claim 1 in combination with an implantable pacemaker cardioverter/defibrillator device.

21. A dual chamber antitachycardia pacing device according to claim 20 wherein said pacemaker includes at least one of single chamber and dual chamber bradycardia pacing.

22. A dual chamber antitachycardia pacing device according to claim 1 wherein said device includes means for sensing inherent QRS complexes during delivery of said trains of pacing pulses, means for determining an acceleration detection cycle length value less than said tachycardia cycle length, means for measuring the cycle lengths of said sensed QRS complexes, and means for delivering at least one of cardioversion and defibrillation therapy when a programmed number of said cycle lengths of said sensed QRS complexes are less than said acceleration detection cycle length.

23. The dual chamber antitachycardia pacing device according to claim 1 wherein said means for determining an initial value AV delay interval includes programming means for programming said interval.

24. A method of antitachycardia pacing in a dual chamber pacing device comprising the steps of:
    measuring cycle length of the tachycardia,
    determining a VA interval value less than or equal to the tachycardia cycle length,
    determining an initial value of the AV delay interval,
    delivering a pulse to the ventricle,
    delivering a pulse to the atrium at the expiration of said determined VA interval value,
    delivering a pulse to the ventricle at the expiration of said AV interval value,
    repeating pulse delivery to the atrium and the ventricle until the expiration of N VA intervals and N AV intervals thereby completing a first train of pulses,
    delivering a series of M trains of pulses similar to said first train of pulses,
    varying said AV delay interval value from the initial value at least once prior to the completion of said series of M trains of pulses.

25. The method of antitachycardia pacing in a dual chamber pacing device according to claim 24 further comprising the step of confirming the presence of tachycardia prior to commencing antitachycardia pacing.

26. The method of antitachycardia pacing in a dual chamber pacing device according to claim 24 wherein said initial value of the AV delay interval is determined by programming.

27. The method of antitachycardia pacing in a dual chamber pacing device according to claim 24 wherein said determined VA interval is a percentage of the tachycardia cycle length.

28. The method of antitachycardia pacing in a dual chamber pacing device according to claim 27 wherein said percentage is in the range of fifty to one hundred percent.

29. A method of antitachycardia pacing in a dual chamber pacing device according to claim 24 wherein said initial value AV delay interval is incremented at least once prior to said completion of trains to a final value AV delay interval.

30. A method of antitachycardia pacing in a dual chamber pacing device according to claim 29 further comprising the step of storing a previous average AV delay interval during sinus rhythm, wherein said final value AV delay interval is a function of and less than or equal to one hundred percent of the previous stored average AV delay during sinus rhythm.

31. A method of antitachycardia pacing in a dual chamber pacing device according to claim 29 further comprising the step of providing dual chamber overdrive pacing at the completion of said M trains of pulses.

32. A method of antitachycardia pacing in a dual chamber pacing device according to claim 31 further comprising the step of programming a duration of said dual chamber overdrive pacing.

33. A method of antitachycardia pacing in a dual chamber pacing device according to claim 31 further comprising the step of storing a previous average AV delay interval during sinus rhythm wherein said dual chamber overdrive pacing includes an AV delay interval which is a function of and less than or equal to one hundred percent of the previous stored average AV delay during sinus rhythm.

34. A method of antitachycardia pacing in a dual chamber pacing device according to claim 31 further comprising the step of storing a previous average AV delay interval during sinus rhythm wherein said dual chamber overdrive pacing includes a VA interval which is a function of and less than or equal to one hundred percent of the previous stored average VA delay interval during sinus rhythm.

35. A method of antitachycardia pacing in a dual chamber pacing device according to claim 24 wherein said determined VA interval remains fixed during said series of M trains.

36. A method of antitachycardia pacing in a dual chamber pacing device according to claim 24 further comprising varying said VA interval during said series of M trains.

37. A method of antitachycardia pacing in a dual chamber pacing device according to claim 24 wherein said initial value AV delay interval is less than 20 ms.

38. A method of antitachycardia pacing in a dual chamber pacing device according to claim 24 wherein said initial value AV delay interval is less than or equal to 60 ms.

39. A method of antitachycardia pacing in a dual chamber pacing device according to claim 24 wherein N is fixed during said series of M trains.

40. A method of antitachycardia pacing in a dual chamber pacing device according to claim 39 wherein N is between 1 and 10.

41. A method of antitachycardia pacing in a dual chamber pacing device according to claim 24 further comprising varying N during said series of M trains.

42. A method of antitachycardia pacing in a dual chamber pacing device according to claim 41 wherein N is between 1 and 10.

43. A method of antitachycardia pacing in a dual chamber pacing device according to claim 24 wherein M is between 1 and 100.

44. A method of antitachycardia pacing in a dual chamber pacing device according to claim 24 further comprising performing at least one of cardioversion and defibrillation.

45. A method of antitachycardia pacing in a dual chamber antitachycardia pacing device according to claim 44 further comprising providing at least one of single chamber or dual chamber bradycardia pacing.

46. A method of antitachycardia pacing in a dual chamber antitachycardia pacing device according to claim 44 further comprising the steps of sensing inherent QRS complexes during the delivery of said trains of pacing pulses, determining an acceleration detection cycle length value less than said tachycardia cycle length, measuring cycle lengths of said sensed QRS complexes, and delivering at least one of cardioversion and defibrillation therapy when a programmed number of said cycle lengths of said sensed QRS complexes are less than said acceleration detection cycle length.

47. A dual chamber antitachycardia pacing device for the reversion of tachycardias comprising: means for detecting tachycardia, means for measuring cycle length of said tachycardia, pulse generating means responsive to said tachycardia detecting means for generating heart stimulating pulses for the atrium and for the ventricle, said pulse generating means including means for delivering a series of pacing pulse trains, means for sensing inherent QRS complexes during delivery of said trains of pacing pulses, means for determining an acceleration detection cycle length value less than said tachycardia cycle length, means for measuring cycle lengths of said sensed QRS complexes, and means for delivering at least one of cardioversion and defibrillation therapy when a number of said cycle lengths of said sensed QRS complexes are less than said acceleration detection cycle length.

48. A method of antitachycardia pacing in a dual chamber pacing device comprising the steps of:
detecting a tachycardia, measuring cycle length of the tachycardia, delivering trains of antitachycardia pacing pulses to the atrium and to the ventricle, sensing inherent QRS complexes during the delivery of said trains of pacing pulses, determining an acceleration detection cycle length value less than said tachycardia cycle length, measuring cycle lengths of said sensed QRS complexes, and delivering at least one of cardioversion and defibrillation therapy when a number of said cycle lengths of said sensed QRS complexes are less than said acceleration detection cycle length.

* * * * *

UNITED STATES PATENT AND TRADEMARK OFFICE
CERTIFICATE OF CORRECTION

PATENT NO. : 4,998,974
DATED : March 12, 1991
INVENTOR(S) : NORMA LOUISE GILLI

It is certified that error appears in the above-identified patent and that said Letters Patent is hereby corrected as shown below:

On the title page, the inventor is named as David Aker and should read Norma L. Gilli.

In the Abstract, line 2, "duel" should read --dual--.

In the Abstract, line 11, "train pulses" should read ----train of pulses--.

Column 12, line 18, "16" should read --17--.

Column 12, between lines 44 and 45, insert --detecting a tachycardia;-- before "measuring cycle length of the tachycardia".

Signed and Sealed this

Fourteenth Day of July, 1992

Attest:

DOUGLAS B. COMER

Attesting Officer

Acting Commissioner of Patents and Trademarks